United States Patent
Dollings

[11] Patent Number: 6,063,815
[45] Date of Patent: May 16, 2000

[54] BENZOPENONES USEFUL IN THE TREATMENT OF INSULIN RESISTANCE AND HYPERGLYCEMIA

[75] Inventor: Paul J. Dollings, Newtown, Pa.

[73] Assignee: American Home Products Corporation, Madison, N.J.

[21] Appl. No.: 09/307,920

[22] Filed: May 10, 1999

Related U.S. Application Data

[60] Provisional application No. 60/100,427, May 12, 1998.

[51] Int. Cl.$^7$ .................. A61K 31/24; A61K 31/195; A61K 31/135; A61K 31/12; C07C 229/00
[52] U.S. Cl. .................. 514/535; 514/543; 514/545; 514/561; 514/571; 514/648; 514/687; 560/43; 560/52; 562/433; 562/441; 564/326; 568/31; 568/333
[58] Field of Search ...................... 562/433, 441; 514/561, 571, 687, 648, 535, 543, 545; 568/31, 333; 564/326; 560/43, 52

[56] References Cited

U.S. PATENT DOCUMENTS

| | | |
|---|---|---|
| 3,666,473 | 5/1972 | Colom . |
| 4,223,039 | 9/1980 | Rose et al. ........................ 562/456 |
| 4,242,358 | 12/1980 | Majoie ............................. 562/460 |
| 4,244,731 | 1/1981 | Oshio et al. ....................... 71/105 |
| 5,235,064 | 8/1993 | Gapinski . |

FOREIGN PATENT DOCUMENTS

| | | |
|---|---|---|
| 0276064 | 7/1988 | European Pat. Off. . |
| 1249869 | 9/1967 | Germany . |
| 1291197 | 3/1969 | Germany . |
| 2616414 | 10/1977 | Germany . |
| 5815064 | 9/1983 | Japan . |
| 60-17294 | 9/1985 | Japan . |
| 62-36661 | 2/1987 | Japan . |
| 62-36662 | 2/1987 | Japan . |
| 63-16144 | 7/1988 | Japan . |
| 3247655 | 11/1991 | Japan . |
| 6348018 | 12/1994 | Japan . |
| 1293396 | 11/1969 | United Kingdom . |
| 1268321 | 3/1972 | United Kingdom . |
| 9608483 | 3/1996 | WIPO . |
| 9634851 | 11/1996 | WIPO . |

OTHER PUBLICATIONS

Oshio et al, "Plant growth regulator; substituted phenoxyacetates", CA92:71054, 1980.
Mitsubushi et al, "Benzophenone derivatives", CA96:68600, 1982.
Artini, D. et al., Arzneim.–Forsch. (Drug res.), 21:1, 1971, pp. 30–36.
Ayyangar, N.R. et al., Synthesis,Apr. 1991, pp. 322–324.
Darchen, A. et al., J.C.S. Chem. Comm., 1976, p. 820.

(List continued on next page.)

*Primary Examiner*—Deborah C. Lambkin
*Attorney, Agent, or Firm*—Arnold S. Milowsky

[57] ABSTRACT

This invention provides compounds of Formula I having the structure

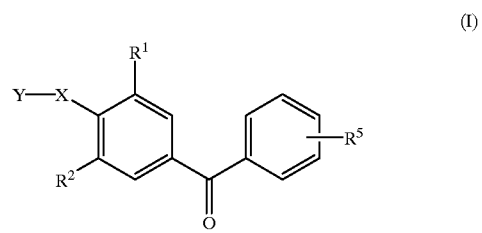

wherein

Y is

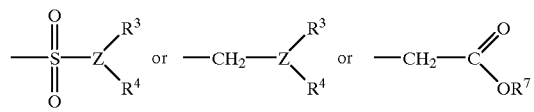

$R^1$ and $R^2$ are each, independently, hydrogen, alkyl of 1–6 carbon atoms, halogen, perfluoroalkyl of 1–6 carbon atoms, cycloalkyl of 3–8 carbon atoms, thienyl, furyl, phenyl or phenyl mono-, di- or tri-substituted with trifluoromethyl, chloro, methoxy, or trifluoromethoxy;

$R^3$ and $R^4$ are each, independently, hydrogen, carboxyl, hydroxyl, hydoxyalkyl of 1–6 carbon atoms, hydroxyalkanoyl of 1–6 carbon atoms, aryloxycarbonyl of 7–13 carbon atoms, alkoxycarbonyl of 2–7 carbon atoms, perfluoroalkoxycarbonyl of 2–7 carbon atoms, alkyl of 1–6 carbon atoms, perfluoroalkyl of 1–6 carbon atoms, aminoalkyl of 1–6 carbon atoms, alkylamino of 1–6 carbon atoms, dialkylamino of 1–6 carbon atoms per alkyl group, tetrazolyl, mercapto, alkylsulfanyl of 1–6 carbon atoms, nitrile, nitro, amino, —$NHSO_2CF_3$, carbamoyl, carboxyaldehyde, halogen, acyl of 1–6 carbon atoms, acylamino of 1–6 carbon atoms, 3-hydroxycyclobut-3-ene-4-yl-1,2-dione, pyridyl, isoxazolyl, pyrimidyl or pyrimidyl substituted with mercapto, tetronic acid, —$OCOR^8$, —$OR^8$ $R^8$ is aryl of 6–12 carbon atoms, aralkyl of 7–13 carbon atoms, monocyclic or bicyclic heteroaryl or a monocyclic or bicyclic heteroaralkyl, alkyl of 1–6 carbon atoms, perfluoroalkyl of 1–6 carbon atoms;

$R^5$ is hydrogen, alkyl of 1–6 carbon atoms, perfluoroalkyl of 1–6 carbon atoms, alkoxy of 1–6 carbon atoms, perfluoroalkoxy of 1–6 carbon atoms, or halogen;

X is —$CH_2NR^6$—, —$NR^6$—, or O;

$R^6$ and $R^7$ are each, hydrogen or alkyl of 1–6 carbon atoms;

Z is phenyl, naphthyl, or a pharmaceutically acceptable salt thereof, which are useful in treating metabolic disorders related to insulin resistance or hyperglycemia.

15 Claims, No Drawings

OTHER PUBLICATIONS

De Cointet, P. et al., Chimie Therapeutique, 5, Sep.–Oct. 1973, pp. 574–587.

Hamacher, H., Arch. Pharmaz., pp. 290–301.

Massolini, G. et al., Il Farmaco, 45(2), 1990, pp. 263–268.

Miyaura, N. et al., Synthetic Communications, 11:7, 1981, pp. 513–519.

Barraclough, P. et al., Arch. Pharm., 323, 1990, pp. 507–512.

Liebeskind, L. S. et al., J. Org. Chem., 55, 1990, pp. 5359–5364.

BENZOPENONES USEFUL IN THE TREATMENT OF INSULIN RESISTANCE AND HYPERGLYCEMIA

This application claims the benefit of U.S. Provisional Application Ser. No. 60/100,427, which was converted from U.S. Patent Application Ser. No. 09/076,419, filed May 12, 1998, pursuant to a petition filed under 37 C.F.R. 1.53(c)(2)(i) on Jul. 6, 1998.

BACKGROUND OF THE INVENTION

The prevalence of insulin resistance in glucose intolerant subjects has long been recognized. Reaven et al (*American Journal of Medicine* 1976, 60, 80) used a continuous infusion of glucose and insulin (insulin/glucose clamp technique) and oral glucose tolerance tests to demonstrate that insulin resistance existed in a diverse group of nonobese, nonketotic subjects. These subjects ranged from borderline glucose tolerant to overt, fasting hyperglycemia. The diabetic groups in these studies included both insulin dependent (IDDM) and noninsulin dependent (NIDDM) subjects.

Coincident with sustained insulin resistance is the more easily determined hyperinsulinemia, which can be measured by accurate determination of circulating plasma insulin concentration in the plasma of subjects. Hyperinsulinemia can be present as a result of insulin resistance, such as is in obese and/or diabetic (NIDDM) subjects and/or glucose intolerant subjects, or in IDDM subjects, as a consequence of over injection of insulin compared with normal physiological release of the hormone by the endocrine pancreas.

The association of hyperinsulinemia with obesity and with ischemic diseases of the large blood vessels (e.g. atherosclerosis) has been well established by numerous experimental, clinical and epidemiological studies (summarized by Stout, *Metabolism* 1985, 34, 7, and in more detail by Pyorala et al, *Diabetes/Metabolism Reviews* 1987, 3, 463). Statistically significant plasma insulin elevations at 1 and 2 hours after oral glucose load correlates with an increased risk of coronary heart disease.

Since most of these studies actually excluded diabetic subjects, data relating the risk of atherosclerotic diseases to the diabetic condition are not as numerous, but point in the same direction as for nondiabetic subjects (Pyorala et al). However, the incidence of atherosclerotic diseases in morbidity and mortality statistics in the diabetic population exceeds that of the nondiabetic population (Pyorala et al; Jarrett *Diabetes/Metabolism Reviews* 1989,5, 547; Harris et al, Mortality from diabetes, in *Diabetes in America* 1985).

The independent risk factors obesity and hypertension for atherosclerotic diseases are also associated with insulin resistance. Using a combination of insulin/glucose clamps, tracer glucose infusion and indirect calorimetry, it has been demonstrated that the insulin resistance of essential hypertension is located in peripheral tissues (principally muscle) and correlates directly with the severity of hypertension (DeFronzo and Ferrannini, *Diabetes Care* 1991, 14, 173). In hypertension of the obese, insulin resistance generates hyperinsulinemia, which is recruited as a mechanism to limit further weight gain via thermogenesis, but insulin also increases renal sodium reabsorption and stimulates the sympathetic nervous system in kidneys, heart, and vasculature, creating hypertension.

It is now appreciated that insulin resistance is usually the result of a defect in the insulin receptor signaling system, at a site post binding of insulin to the receptor. Accumulated scientific evidence demonstrating insulin resistance in the major tissues which respond to insulin (muscle, liver, adipose), strongly suggests that a defect in insulin signal transduction resides at an early step in this cascade, specifically at the insulin receptor kinase activity, which appears to be diminished (reviewed by Haring, *Diabetalogia* 1991, 34, 848).

Protein-tyrosine phosphatases (PTPases) play an important role in the regulation of phosphorylation of proteins. The interaction of insulin with its receptor leads to phosphorylation of certain tyrosine molecules within the receptor protein, thus activating the receptor kinase. PTPases dephosphorylate the activated insulin receptor, attenuating the tyrosine kinase activity. PTPases can also modulate post-receptor signaling by catalyzing the dephosphorylation of cellular substrates of the insulin receptor kinase. The enzymes that appear most likely to closely associate with the insulin receptor and therefore, most likely to regulate the insulin receptor kinase activity, include PTP1B, LAR, PTPα and SH-PTP2 (B. J. Goldstein, *J. Cellular Biochemistry* 1992, 48, 33; B. J. Goldstein, *Receptor* 1993, 3, 1–15,; F. Ahmad and B. J. Goldstein Biochim. *Biophys Acta* 1995, 1248, 57–69).

McGuire et al. (*Diabetes* 1991, 40, 939), demonstrated that nondiabetic glucose intolerant subjects possessed significantly elevated levels of PTPase activity in muscle tissue vs. normal subjects, and that insulin infusion failed to suppress PTPase activity as it did in insulin sensitive subjects.

Meyerovitch et al (*J. Clinical Invest.* 1989, 84, 976) observed significantly increased PTPase activity in the livers of two rodent models of IDDM, the genetically diabetic BB rat, and the STZ-induced diabetic rat. Sredy et al (*Metabolism,* 44, 1074, 1995) observed similar increased PTPase activity in the livers of obese, diabetic ob/ob mice, a genetic rodent model of NIDDM.

The compounds of this invention have been shown to inhibit human-derived recombinant PTPase-1B (hPTP-1B) in vitro. They are useful in the treatment of insulin resistance associated with obesity, glucose intolerance, diabetes mellitus, hypertension and ischemic diseases of the large and small blood vessels.

M. Fortin, et al. (WO 96/08483) discloses the sulfonyl ester A as an agent for the treatment of endothelin hypertension, vascular contraction, post cerebral hemorrhage, renal deficiencies, myocardial infarction and as a post angioplatsy antirestonic agent.

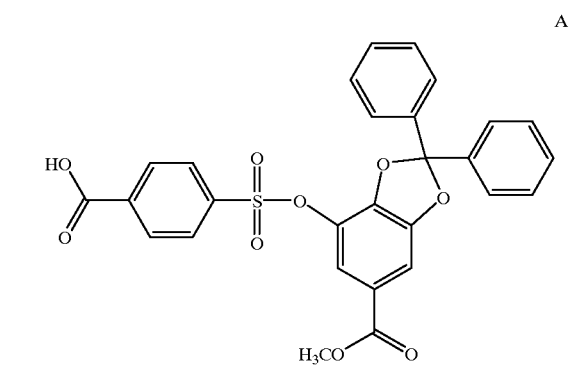

A

W. R. Baker, et al. (WO 96/34851) discloses the sulfonamide B as an inhibitor of squalene synthetase and protein farnesyltransferase.

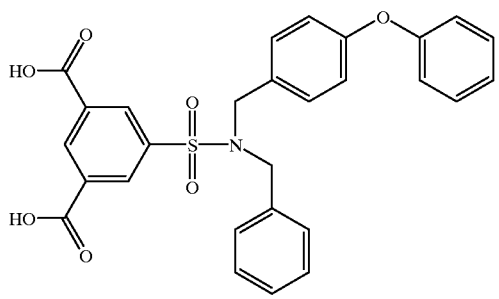

D. M. Gapinski (EP 276 064 & U.S. Pat. No. 5,235,064) discloses the benzenepropanoic acid C as a leukotriene antagonist.

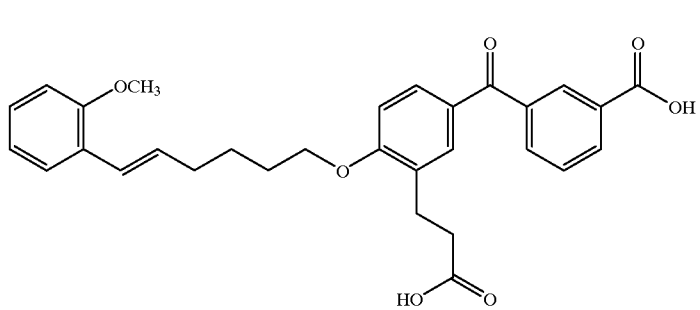

N. R. Ayyangar, et al., *Synthesis* 1991, *Issue* 4, 322–324 prepared D (R is —CH$_3$; R' and R" is H) using (trichloromethyl)benzene. D. Artini, et al, *Arzneim.-Forsch.* 1971, 21(1), 30–36 also utilized D (R is —CH$_3$, R' and R" is H) as an intermediate to prepare analgesic and anitinflammatory compounds. A. Darchen, et al., *J. Chem. Soc., Chem. Commun.* 1976, *Issue* 20, 820 disclosed D (R and R" is H, R' is —OH). H. Hamacher, *Arch. Pharm.* (*Weinheim, Ger.*) 1975, 308(4), 290–301 utilized D (R and R' is H, R" is —OCH$_3$) as an intermediate for the preparation of N-arylsubstituted derivatives of cyclophosphamide.

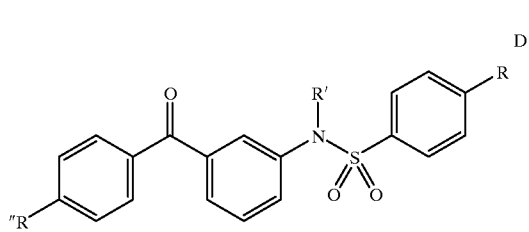

Several patents (JP 06348018, JP 03247655, JP 63161449, JP 62036661, JP 62036662, JP 58150948, U.S. Pat. No. 3,666,473, GB 1293396, DE 1291197, DE 660708) disclose compounds E and F and hydroxylated derivatives in photosensitive resin compositions.

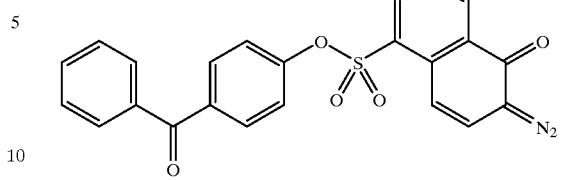

-continued

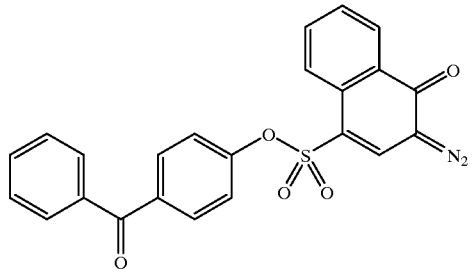

K. Katsuhiko et al., (JP 60172946 A2) disclosed the fluorine containing benzophenone G (R is alkyl, halo, cycloalkyl; R$^1$ is (substituted)phenyl) to be used as a herbicide.

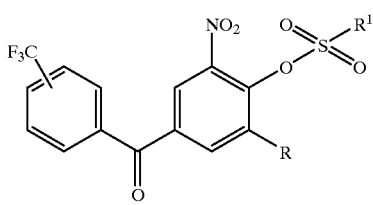

T. Takeo (DE 1249869) disclosed the sulfonamide H for the treatment of malignant tumors.

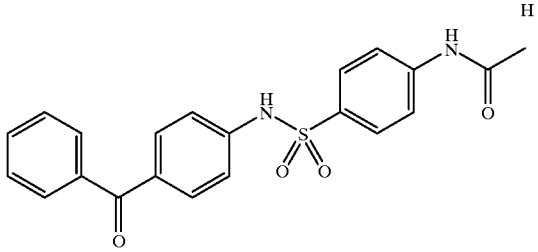

G. Massolini et al., Farmaco 45: 263 (1990) disclosed the compound I as a herbicide.

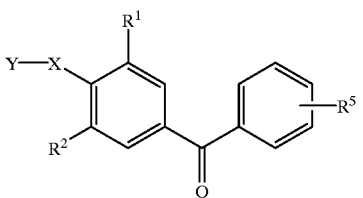

F. Alfes et al., (DE 2616414 A1) discloses the hydroxylated benzophenone J where $R^1$ is alkyl or alkylamino.

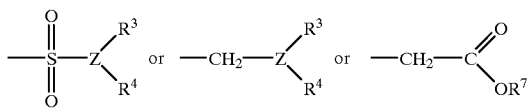

DESCRIPTION OF THE INVENTION

This invention provides a compound of formula I having the structure wherein
Y is $R^1$ and $R^2$ are each, independently, hydrogen, alkyl of 1–6 carbon atoms, halogen, perfluoroalkyl of 1–6 carbon atoms, cycloalkyl of 3–8 carbon atoms, thienyl, furyl, phenyl or phenyl mono-, di- or tri-substituted with trifluoromethyl, chloro, methoxy, or trifluoromethoxy;

$R^3$ and $R^4$ are each, independently, hydrogen, carboxyl, hydroxyl, hydoxyalkyl of 1–6 carbon atoms, hydroxyalkanoyl of 1–6 carbon atoms, aryloxycarbonyl of 7–13 carbon atoms, alkoxycarbonyl of 2–7 carbon atoms, perfluoroalkoxycarbonyl of 2–7 carbon atoms, alkyl of 1–6 carbon atoms, perfluoroalkyl of 1–6 carbon atoms, aminoalkyl of 1–6 carbon atoms, alkylamino of 1–6 carbon atoms, dialkylamino of 1–6 carbon atoms per alkyl group, tetrazolyl, mercapto, alkylsulfanyl of 1–6 carbon atoms, nitrile, nitro, amino, $-NHSO_2CF_3$, carbamoyl, carboxyaldehyde, halogen, acyl of 1–6 carbon atoms, acylamino of 1–6 carbon atoms, 3-hydroxy-cyclobut-3-ene-4-yl-1,2-dione, pyridyl, isoxazolyl, pyrimidyl or pyrimidyl substituted with mercapto, tetronic acid, $-OCOR^8$, $-OR^8$ $R^8$ is aryl of 6–12 carbon atoms, aralkyl of 7–13 carbon atoms, monocyclic or bicyclic heteroaryl or a monocyclic or bicyclic heteroaralkyl, alkyl of 1–6 carbon atoms, perfluoroalkyl of 1–6 carbon atoms;

$R^5$ is hydrogen, alkyl of 1–6 carbon atoms, perfluoroalkyl of 1–6 carbon atoms, alkoxy of 1–6 carbon atoms, perfluoroalkoxy of 1–6 carbon atoms, or halogen;

X is $-CH_2NR^6-$, $-NR^6-$, or O;

$R^6$ and $R^7$ are each, hydrogen or alkyl of 1–6 carbon atoms;

Z is phenyl, pyridyl, naphthyl, thienyl, furyl, pyrrolyl, pyrazolyl, isoxazolyl, or isothiazolyl, or a pharmaceutically acceptable salt thereof, which are useful in treating metabolic disorders related to insulin resistance or hyperglycemia.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

The terms alkyl, alkoxy, alkanoyl used alone or in conjunction with another term are defined as branched or straight chained optionally substituted with fluorine. The term cycloalkyl may be optionally substituted with fluorine. Halogen means bromine, chlorine, fluorine, and iodine.

It is preferred that the aromatic portion of the terms aryl, aralkyl, arylalkoxy, aryloxy, aroyloxy, or aryloxycarbonyl substituent is a phenyl, naphthyl or 1,4-benzodioxan-5-yl group, with phenyl being most preferred. The aryl moiety may be optionally mono-, di-, or tri- substituted with a substituent selected from the group consisting of alkyl of 1–6 carbon atoms, alkylsulfanyl of 1–6 carbon atoms, alkoxy of 1–6 carbon atoms, trifluoromethyl, halogen, mercapto, alkoxycarbonyl of 2–7 carbon atoms, alkylamino of 1–6 carbon atoms, and dialkylamino in which each of the alkyl groups is of 1–6 carbon atoms, nitro, cyano, $-CO_2H$, alkylcarbonyloxy of 2–7 carbon atoms, and alkylcarbonyl of 2–7 carbon atoms.

The heteroaromatic portion of the terms heteroaryl, heteroaralkyl and heteroaryloxycarbonyl are defined as a stable 5 to 10 member mono or bicyclic heterocyclic ring system which consists of carbon atoms and from 1 to 3 heteroatoms selected from N, O and S and selected from the group consisting of quinoline, isoquinoline, pyridine, indole, isoindole, pyrrole, quinazoline, oxazole, oxazine, isoxazole, isothiazole, pyrazine, pyridazine, pyrimidine, thiophene, furan, benzofuran, benzimidazole, benzoxadiazole, pyrazole, pyrrolidinone, benzoxazole, benzpyrazzole, benzisoxazole, thiazole, thiadiazole, triazole, isobenzothiophene and benzothiophene. The heteroaromatic group may be optionally mono-, di-, or tri- substituted with a substituent selected from the group consisting of alkyl of 1–6 carbon atoms, alkylsulfanyl of 1–6 carbon atoms, alkoxy of 1–6 carbon atoms, trifluoromethyl, halogen, mercapto, alkoxycarbonyl of 2–7 carbon atoms, alkylamino of 1–6 carbon atoms, dialkylamino in which each of the alkyl groups is of 1–6 carbon atoms, nitro, cyano, —$CO_2H$, alkylcarbonyloxy of 2–7 carbon atoms, and alkylcarbonyl of 2–7 carbon atoms.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers, as well as the racemic and resolved, enantiomerically pure R and S stereoisomers, as well as other mixtures of the R and S stereoisomers and pharmaceutically acceptable salts thereof.

Preferred compounds of this invention are those compounds of Formula I, wherein $R^3$ and $R^4$ are independent from each other, hydrogen, carboxyl, hydroxyl, halogen, alkoxycarbonyl of 2–7 carbon atoms, aryloxycarbonyl of 7–13 carbon atoms, alkyl of 1–6 carbon atoms, hydroxyalkyl of 1–6 carbon atoms, perfluoroalkyl of 1–6 carbon atoms, tetrazolyl, mercapto, nitrile, amino, —$NHSO_2CF_3$, carbamoyl, carboxyaldehyde, acyl of 1–6 carbon atoms, acylamino, pyridyl, isoxazolyl, pyrimidyl, pyrimidyl substituted with mercapto, —$OCOR^8$, or —$OR^8$;

$R^5$ is hydrogen, alkoxy of 1–6 carbon atoms, perfluoroalkoxy of 1–6 carbon atoms, or halogen;

$R^6$ is hydrogen

X is —$CH_2NR^6$—, —$NR^6$—, or O;

Z is phenyl, thienyl, or pyrazolyl;

or a pharmaceutically acceptable salt thereof.

More preferred compounds of this invention are those compounds of Formula I, wherein $R^1$ and $R^2$ are each, independently, hydrogen, iodo, phenyl, or thienyl;

$R^3$ and $R^4$ are each, independently, hydrogen, carboxyl, or hydroxyl;

$R^5$ is hydrogen, alkoxy of 1–6 carbon atoms, or halogen;

X is O;

Z is phenyl;

or a pharmaceutically acceptable salt thereof.

Specifically preferred compounds of the present invention are set forth below:

EXAMPLE 1
(5'-Benzoyl-[1,1';3',1"]terphenyl-2'-yloxy)-acetic acid;

EXAMPLE 2
4-(5'-Benzoyl-[1,1';3',1"]terphenyl-2'-yloxymethyl)-2-hydroxy-benzoic acid;

EXAMPLE 3
2-Acetoxy-5-(4-benzoyl-2,6-diiodo-phenoxymethyl)-benzoic acid methyl ester;

EXAMPLE 4
4-(5'-Benzoyl-[1,1';3',1"]terphenyl-2'-yloxysulfonyl)-2-hydroxy-benzoic acid;

EXAMPLE 5
4-(5'-Benzoyl-[1,1';3',1"]terphenyl-2'-yloxysulfonyl)-2-hydroxy-benzoic acid ethyl ester;

EXAMPLE 6
2-Hydroxy-4-[4-(4-methoxy-benzoyl)-phenoxysulfonyl]-benzoic acid;

EXAMPLE 7
4-[2,6-Diiodo-4-(4-methoxy-benzoyl)-phenoxysulfonyl]-2-hydroxy-benzoic acid;

EXAMPLE 8
2-Hydroxy-4-[5'-(4-methoxy-benzoyl)-[1,1';3',1"]terphenyl-2'-yloxysulfonyl)-benzoic acid;

EXAMPLE 9
4-(4-Benzoyl-2,6-di-thiophen-3-yl-phenoxysulfonyl)-2-hydroxy-benzoic acid;

EXAMPLE 10
4-(5'-Benzoyl-[1,1';3',1"]terphenyl-2'-yloxysulfonyl)-benzoic acid;

EXAMPLE 11
4-[5-(2-Chloro-benzoyl)-biphenyl-2-yloxysulfonyl]-2-hydroxy-benzoic acid;

EXAMPLE 12
4-(4-Benzoyl-2,6-diiodo-phenoxysulfonyl)-2-hydroxy-benzoic acid;

or a pharmaceutically acceptable salt thereof.

The compounds of this invention were prepared according to the following schemes from commercially available starting materials or starting materials which can be prepared using to literature procedures. These schemes show the preparation of representative compounds of this invention.

The compounds of this invention can be prepared according to the methods outlined in the schemes below:

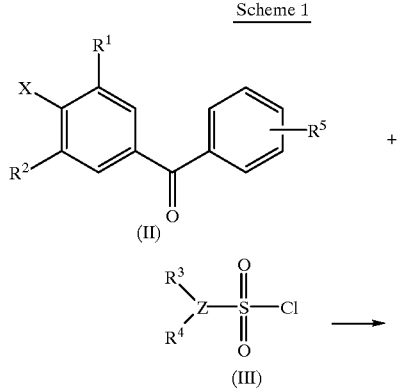

-continued

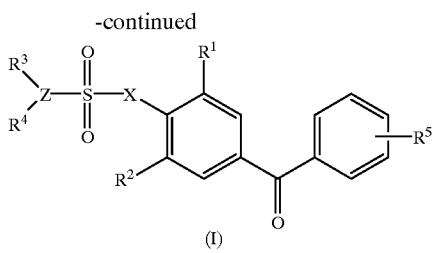

(I)

The preparation of sulfonyl ester derivatives of formula (I) is described in Scheme 1. Starting with synthetically prepared or commercially available 4-hydroxybenzophenones (II: X=OH), the compounds of formula (I) can be prepared by sulfonylation on the phenolic oxygen using one or more molar equivalents of suitable sulfonylating (III) agent to provide the sulfonic acid esters of formula (I). The sulfonylating (III) agent is generally a aryl or heteroaryl sulfonic acid chloride. The reaction is run under standard conditions using a suitable base such sodium hydride, pyridine or Tris base in an appropriate solvent such as dichloromethane, THF or $H_2O$ at temperatures ranging from 0° C. to ambient temperature. The starting sulfonyl chloride is commercially available or can be easily prepared by known procedures. The aryl or heteroaryl sulfonic acid chloride can be prepared by reacting the aryl or heteroaryl sulfonic acid with one or more molar equivalents of oxalyl chloride or thionyl chloride, in a suitable solvent such as dichloromethane, chloroform or diethyl ether, to afford the aryl or heteroaryl sulfonic acid chloride. This reaction is often catalyzed by adding small amounts (0.01 to 0.1 molar equivalents) of dimethylformamide. Alternatively, the sulfonyl chlorides can prepared using a modification of Barraclough, et al., *Arch. Pharm.* (*Weinheim*) 1990, 323, 507. Thus, the aniline of commercially available 4-aminosalicylic acid sodium salt dihydrate is diazotized with sodium nitrite in HOAc/HCl at −10° C. and the subsequent the diazonium salt can converted to the sulfonyl chloride by introduction of sulfur dioxide into the reaction in the presence of copper (I) chloride.

The groups $R^3$ and $R^4$ connected to Z can be further derivatized. For example, when $R^3$ or $R^4$ is an ester of a carboxylic acid or alcohol the compound can be transformed into the respective carboxylic acid or alcohol analog using standard conditions. The conditions to effect these transformations include aqueous base in which one or more molar equivalents of alkali metal hydroxide such as sodium hydroxide is used in water with a co-solvent such as THF, dioxane or a lower alcohol such as methanol or mixtures of THF and a lower alcohol at temperatures ranging from 0° C. to 40° C. Acidic conditions to effect the ester to acid conversion include using trifluoroacetic acid in a suitable solvent such as dichloromethane. When $R^3$ or $R^4$ is a carboxcylic acid or ester the compound can be reduced to the respective primary alcohol analog using standard conditions such as lithium aluminum hydride. When $R^3$ or $R^4$ is an aldehyde or ketone the compound can be reduced to the respective alcohol analog using a metal catalyst, by sodium in alcohol, sodium borohydride and by lithium aluminum hydride. When $R^3$ and $R^4$ is an ether, the compound can be transformed to the free alcohol by using one to ten molar equivalents of a strong Lewis acid such as a trihaloborane, most conveniently tribromoborane in a halocarbon solvent such as dichloromethane. When $R^3$ or $R^4$ is an alcohol the compound can be oxidized to the respective aldehyde, carboxylic acid or ketone analog using a transition metal oxidant (chromium trioxide-pyridine, pyridinium chlorochromate, manganese dioxide) in an inert solvent such as ether, dichloromethane. Alcohols can also be oxidized using DMSO with a number of electrophilic molecules (dicyclohexylcarbodiimide, acetic anhydride, trifluoro acetic anhydride, oxalyl chloride and sulfur dioxide). When $R^3$ or $R^4$ is a carboxcylic acid the compound can be transformed into a carboxylic acid amide analog. This transformation can be accomplished using standard methods to effect carboxylic acid to carboxylic acid amide transformations. These methods include converting the acid to an activated acid and reacting with one or more molar equivalents of the desired amine. Amines in this category include ammonia in the form of ammonium hydroxide, hydroxyl amine and 2-aminopropionitrile. Methods to activate the carboxylic acid include reacting said acid with one or more molar equivalents of oxalyl chloride or thionyl chloride to afford the carboxylic acid chloride in a suitable solvent such as dichloromethane, chloroform or diethyl ether. This reaction is often catalyzed by adding small amounts (0.01 to 0.1 molar equivalents) of dimethylformamide. Other methods to activate the carboxylic acid include reacting said acid with one or more molar equivalents dicyclohexylcarbodiimide with or without one or more molar equivalents of hydroxybenzotriazole in a suitable solvent such as dichloromethane or dimethylformamide at temperatures ranging from 0° C. to 60° C. When $R^3$ or $R^4$ is a carboxcylic acid, the compound can be esterified utilizing an alkyl or alkyl trichloroacetimidate with or without a catalyst such as $BF_3Et_2O$ or methanesulfonic acid in a suitable solvent such as dichloromethane, ethyl acetate or cyclohexane. When $R^3$ or $R^4$ is nitro, the compound can be reduced to the respective amino compound most readily using tin dichloride in ethylacetate at 40° C. to 100° C. or with hydrazine and Montmorillinite clay in ethanol at 40° C. to 100° C. or by catalytic hydrogenation in the presence of a catalyst such as palladium on carbon. When $R^3$ or $R^4$ is an amine or an alcohol, the compound can be acylated using one or more molar equivalents of suitable acylating agent. The acylating agent is generally a lower alkyl or aryl carboxylic acid anhydride or a lower alkyl or aryl carboxylic acid chloride. The reaction is run under standard conditions, for example the use of pyridine as solvent with or without a co-solvent such as dichloromethane at 0° C. to room temperature. When $R^3$ or $R^4$ is an alcohol, the compound can be alkylated under the conditions of the Mitsunobu Reaction (for a review see Oyo Mitsunobu *Synthesis*. 1981, 1–27). The other co-reagents necessary to effect the Mitsunobu Reaction include one or more molar equivalents of a lower alkyl azodicarboxylate diester such as diethyl azodicarboxylate and one or more molar equivalents of triarylphosphine such as triphenylphosphine in a suitable solvent such as diethyl ether, THF, benzene or toluene at temperatures ranging from −20° C. to 120° C. When $R^3$ or $R^4$ is an alcohol it can be acylated with a lower alkyl or aryl carboxylic acid anhydride in the presence of magnesium iodide in diethyl ether at ambient temperature to reflux. When $R^3$ or $R^4$ is a nitrile it can be reduced to the aminoalkyl compound by tin (II) chloride in refluxing ethyl acetate or by catalytic hydrogenation in the presence of a catalyst such as Raney nickel or by lithium aluminum hydride in an inert solvent such as ether. When $R^3$ or $R^4$ is a nitrile it can be converted to a carboxylic acid amide using standard conditions such as $HCl/H_2O$ at ambient temperatures to reflux or a milder procedure involves the reaction of the nitrile with an alkaline solution of hydrogen peroxide. When $R^3$ or $R^4$ is halogen or trifluoromethanesulfonate it can be converted to a 3-hydroxy-cyclobut-3-ene-4-yl-1,2-dione by methodology of Liebeskind et. al. (*J.*

*Org. Chem.* 1990, 55, 5359). When $R^3$ or $R^4$ is an alcohol can be alkylated with a suitable alkylating agent such as one or more molar equivalents of alkyl halide in the presence a base such as potassium carbonate or sodium hydroxide in a suitable solvent such as THF, DMF or DMSO at temperatures ranging from 0° C. to 60° C. When $R^3$ or $R^4$ is a carboxcylic acid, the compound can be coupled to tetronic acid with a coupling reagent such as 1-(3-dimethylaminopropyl)-3-ethylcarbodiimide in the presence of a base such as triethylamine or DMAP in a suitable solvent such as DMF.

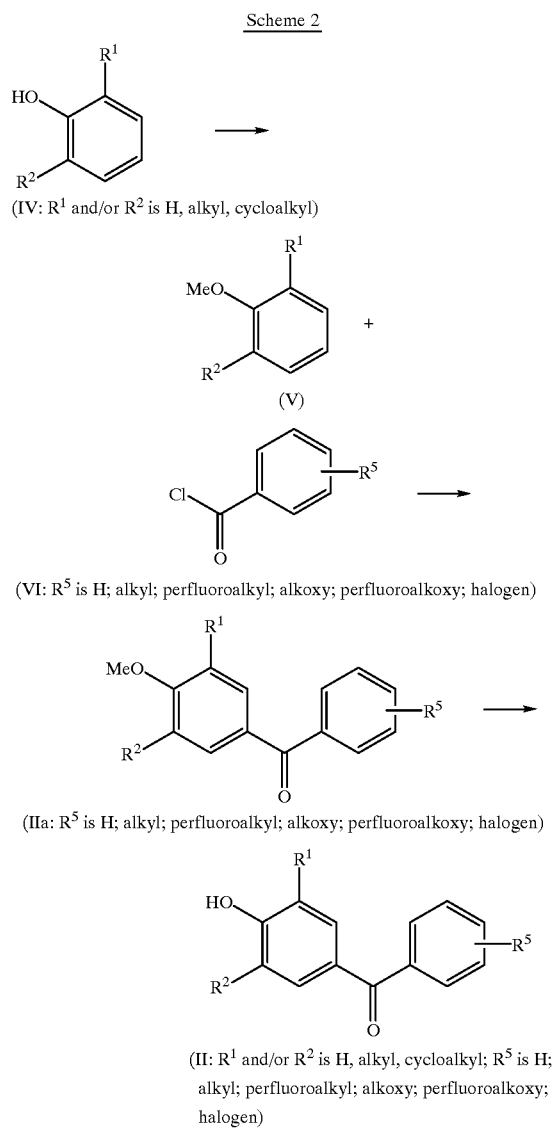

Derivatives of hydroxybenzophenones of formula (II: $R^1$ and/or $R^2$ is alkyl, cycloalkyl; $R^5$ is H, alkyl; perfluoroalkyl; alkoxy; perfluoroalkoxy; halogen) can be prepared as in Scheme 2. The commercially available 2,6-(mono or disubstituted)phenols of formula (IV: $R^1$ and/or $R^2$ is alkyl, cycloalkyl) can be methylated (iodomethane/potassium carbonate/DMF) to give compound the methyl ether compound (V), acylated in the 4-position with a desired benzoic acid chloride (VI: $R^5$ is H, alkyl; perfluoroalkyl; alkoxy; perfluoroalkoxy; halogen) in the presence of aluminum chloride in an inert solvent such as dichloromethane, generally at ambient temperature to yield compound (IIa: $R^1$ and/or $R^2$ is alkyl, cycloalkyl; $R^5$ is H, alkyl; perfluoroalkyl; alkoxy; perfluoroalkoxy; halogen). The compound methyl ether benzophenone (IIa: $R^1$ and/or $R^2$ is alkyl, cycloalkyl; $R^5$ is H, alkyl; perfluoroalkyl; alkoxy; perfluoroalkoxy; halogen) can be transformed to the free phenol by using one to ten molar equivalents of a strong Lewis acid such as a trihaloborane, most conveniently tribromoborane in a halocarbon solvent such as dichloromethane to give compounds of formula (II: $R^1$ and/or $R^2$ is alkyl, cycloalkyl; $R^5$ is H, alkyl; perfluoroalkyl; alkoxy; perfluoroalkoxy; halogen).

The benzoic acid chloride (VI: $R^5$ is H, alkyl; perfluoroalkyl; alkoxy; perfluoroalkoxy; halogen) is prepared from the corresponding benzoic acid by standard procedures using reagents such as oxalyl chloride and thionyl chloride. The starting benzoic acid of the benzoic acid chloride (VI $R^5$ is H, alkyl; perfluoroalkyl; alkoxy; perfluoroalkoxy; halogen) is commercially available or can be easily prepared by known procedures.

All the compounds prepared in Scheme 2 of formula (II: $R^1$ and/or $R^2$ is alkyl, cycloalkyl; $R^5$ is H, alkyl; perfluoroalkyl; alkoxy; perfluoroalkoxy; halogen) can be utilized in other schemes to prepared compounds of formula (I). For example, the prepared compound (II: $R^1$ and/or $R^2$ is alkyl, cycloalkyl; $R^1$ is H, alkyl; perfluoroalkyl; alkoxy; perfluoroalkoxy; halogen) can be used in Scheme 1 to prepared sulfonyl esters of formula (I: $R^1$ and/or $R^2$ is alkyl, cycloalkyl; $R^5$ is H, alkyl; perfluoroalkyl; alkoxy; perfluoroalkoxy; halogen). All the compounds prepared in Scheme 2 of formula (II: $R^1$ and/or $R^2$ is alkyl, cycloalkyl; $R^5$ is H, alkyl; perfluoroalkyl; alkoxy; perfluoroalkoxy; halogen) can be utilized in Schemes 3 and 4 for further synthetic modifications.

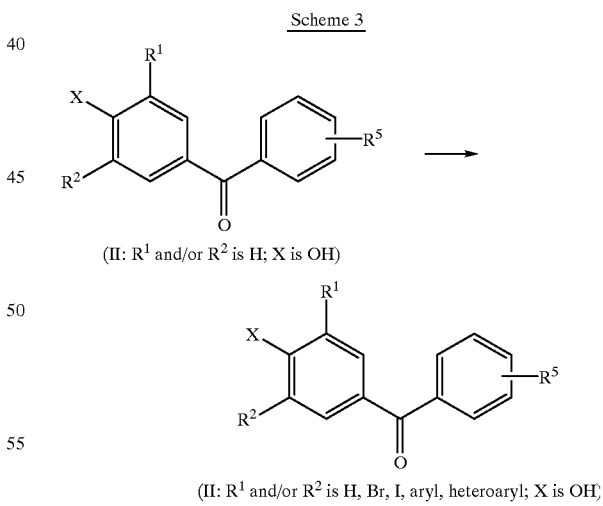

Further derivatives of the compounds of formula (II) in Scheme 3 can be prepared by the following methods. The phenol of formula (II: $R^1$ and/or $R^2$ is H; X is OH) can be conveniently iodinated to the diiodophenol of formula (VI: $R^1$ and $R^2$ is I; X is —OH) using at least two molar equivalents of iodine in the presence of two or more molar equivalents of an alkali metal hydroxide such as NaOH in an alcohol solvent such as methanol at −20° C. to room temperature. Similarly the monoiodophenol (VI: $R^1$ is H; $R^2$ is I; X is OH) can be prepared from the phenol of formula (II: $R^1$ and/or $R^2$ is H; X is OH) using one to 1.5 molar equivalents of iodine in the presence of at least one equivalent of an alkali metal hydroxide such as NaOH in a alcohol solvent such as methanol at −20° C. to room temperature. Either the monoiodophenol (VI: $R^1$ is H; $R^2$ is I; X is OH) or the diiodophenol (VI: $R^1$ and $R^2$ is I; X is OH) can be converted to the respective alkyl ether derivatives of formula (II: $R^1$ and/or $R^2$ is I; X is O-alkyl) by reacting the phenol moiety with a suitable methylating agent such as one or more molar equivalents of MEM chloride, methyl iodide or dimethylsulfate employing a base such sodium hydride or an alkali methyl carbonate or hydroxide such as potassium carbonate or sodium hydroxide in a suitable solvent such as THF, DMF or DMSO. The reaction is generally performed at temperatures ranging from 0° C. to 60° C. The mono or dibrominated derivatives of formula (II: $R^1$ and/or $R^2$ is Br; X is O-alkyl) can be prepared in analogs fashion by substituting bromine for iodine in the sequence above.

The mono or diiodo alkylether derivatives of formula (II: $R^1$ and/or $R^2$ is I; X is O-alkyl) can be reacted with an arylboronic acid or heteroarylboronic acid to afford the product of formula (II: $R^1$ and/or $R^2$ is aryl or heteroaryl; X is O-alkyl) under the conditions of the Suzuki Reaction (*Synthetic Communications* 1981 11(7) 513). The other co-reagents necessary to effect the Suzuki Reaction include one or more molar equivalents of a metal catalyst such as tetrakis(triphenylphosphine)palladium or palladium (II) acetate and a base such as barium hydroxide octahydrate or sodium carbonate in a solvent such as benzene, toluene or DME/$H_2O$. The starting aryl or heteroaryl boronic acids are commercially available or can be prepared by standard synthetic methods. The mono or diaryl or mono or diheteroaryl alkoxy analogs of formula (II: $R^1$ and/or $R^2$ is aryl or heteroaryl; X is O-alkyl) can be converted to the corresponding mono or diaryl or mono or diheteroaryl phenol analogs of formula (II: $R^1$ and/or $R^2$ is aryl or heteroaryl; X is OH) using standard demethylation procedures including one or more molar equivalents of boron tribromide or boron trichloride in dichloromethane at −78° C. to room temperature.

All the compounds prepared in Scheme 3 of formula (II: $R^1$ and/or $R^2$ is H, I, Br, aryl, heteroaryl; X is OH) can be utilized in other schemes to prepare compounds of formula (I). For example, the prepared compound (II: $R^1$ and/or $R^2$ is H, I, Br, aryl, heteroaryl; X is OH) can be used in Scheme 1 to prepared sulfonyl esters of formula (I: $R^1$ and/or $R^2$ is H, I, Br, aryl, heteroaryl). All the compounds prepared in Scheme 3 of formula (II: $R^1$ and/or $R^2$ is H, I, Br, aryl, heteroaryl; X is OH) can be utilized and further modified synthetically in Scheme 4.

Scheme 4

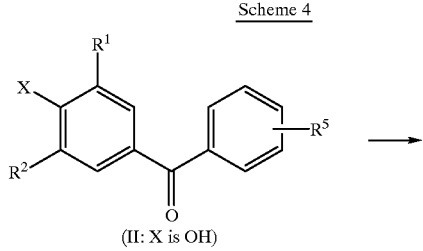

(II: X is OH)

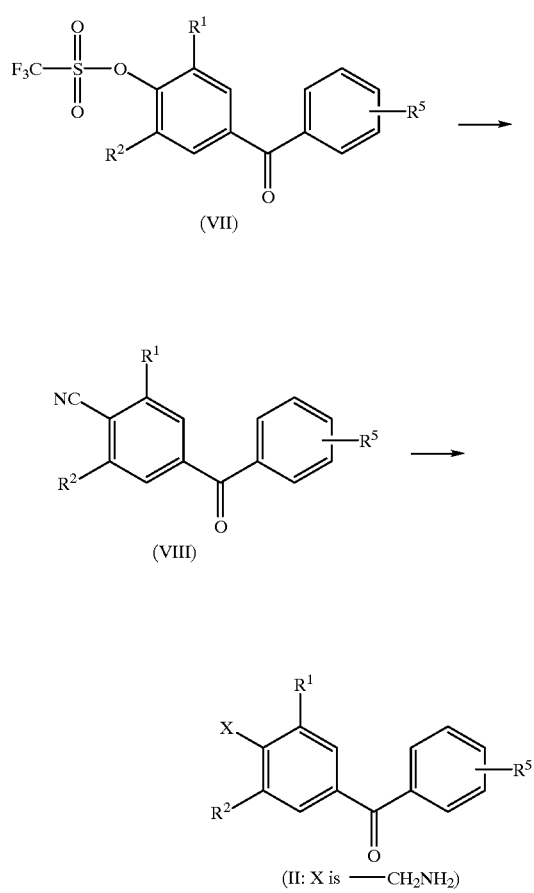

In a three step process (Scheme 4) compounds of formula (II: X is OH) can be converted to compounds of formula (II: X is —$CH_2NH_2$). Reaction of compounds of formula (II: X is OH) with trifluoromethanesulfonic anhydride or trifluoromethanesulfonic acid chloride in the presence of a organic base such as pyridine or triethylamine in dichloromethane at 0° C. to ambient temperature provides compound (VII). The triflate (VII) can be converted to the carbonitrile (VIII) with potassium cyanide or zinc cyanide in the presence of tetrakistriphenylphosphinenickel(O) which can be generated in situ from bistriphenylphosphinenickel (II) bromide and Zn/$PPh_3$. The nitrile (VIII) can be reduced to the aminoalkyl compound (II: X is —$CH_2NH_2$) by tin (II) chloride in refluxing ethyl acetate or by catalytic hydrogenation in the presence of a catalyst such as Raney nickel or by lithium aluminum hydride in an inert solvent such as ether.

The prepared compounds of formula (II: X is —$CH_2NH_2$) can be used in Scheme 1 to prepared sulfonamides of formula (I: X is —$CH_2NH$—).

Scheme 5

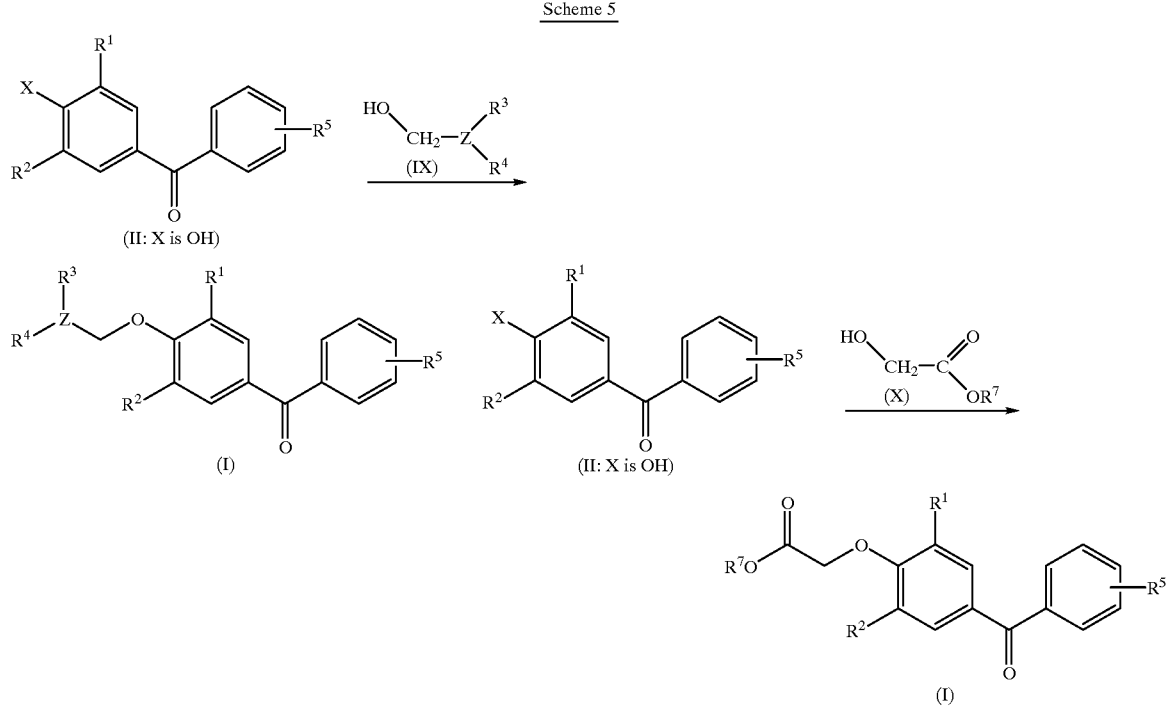

The preparation of ether derivatives of formula (I) is described in Scheme 5. The phenols of formula (II; X is OH) can be reacted with a hydroxyalkylaryl or hydroxyalkylheteroaryl of formula (IX) or a hydroxyalkylester of formula (X) to afford the alkylated product of formula (I) under the conditions of the Mitsunobu Reactions (for a review see Oyo Mitsunobu *Synthesis*. 1981, 1–27). The other co-reagents necessary to effect the Mitsunobu Reaction include one or more molar equivalents of a lower alkyl azodicarboxylate diester such as diethyl azodicarboxylate or diisopropyl azodicarboxylate and one or more molar equivalents of triarylphosphine such as triphenylphosphine in a suitable solvent such as diethyl ether, THF, benzene or toluene at temperatures ranging from −20° C. to 120° C.

The hydroxylalkylester of formula (X) is commercially available. The hydroxyalkylaryl or hydroxyalkylheteroaryl of formula (IX) is either commercially available or prepared synthetically (Scheme 6).

Scheme 6

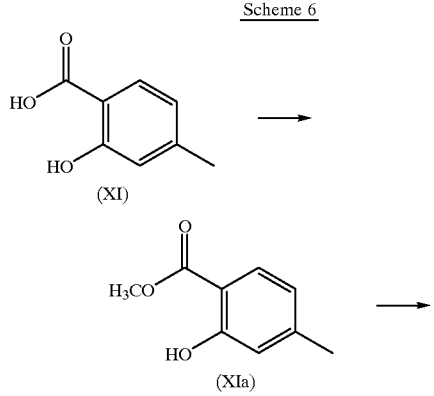

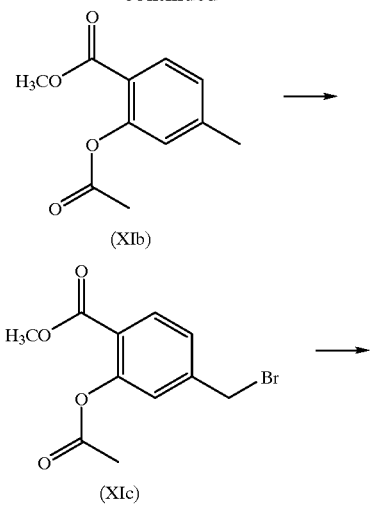

-continued

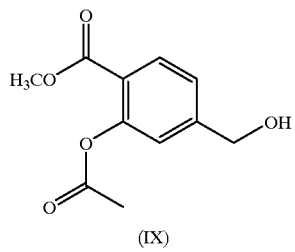

The preparation of hydroxyalkylaryl or hydroxyalkylheteroaryl compounds of formula (IX) is illustrated Scheme 6. The carboxyl of commercially available 4-methylsalicylic acid (XI) is esterified with an alkyl halide such as iodomethane in the presence of a base such as 1,8-diazabicyclo[5.4.0]undec-7-ene (DBU) in an aprotic solvent such as THF to give compound (XIa). The phenol can also be protected as an ester using an acylating agent such as a lower alkyl acid anhydride or a lower alkyl carboxylic acid chloride. The reaction is run under standard conditions, for example the use of pyridine as solvent with or without a co-solvent such as dichloromethane at 0° C. to room temperature to give compound (XIb). The benzylic position of (XIb) can be brominated with N-bromosuccinimide in the presence of azobisisobutyronitrile (AIBN) in a solvent such as benzene with or without ultraviolet irradiation to give compound (XIc). The benzylic bromide can be converted to the benzylic alcohol with sodium formate in a combination solvent of ethanol/dimethyl sulfoxide/$H_2O$ at temperatures ranging from 50° C. to reflux to give the desired hydroxyalkylaryl (IX).

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of compounds of this invention to treat or inhibit disorders related to insulin resistance or hyperglycemia was established with representative compounds of this invention in the following standard pharmacological test procedure which measures the inhibition of PTPase.

Inhibition of Tri-Phosphorylated Insulin Receptor Dodecaphosphopeptide Dephosphorylation by hPTP1B This standard pharmacological test procedure assesses the inhibition of recombinant, human protein tyrosine phosphatase (PTP) 1B activity. The substrate for the PTPase assay is a dodecaphosphopeptide corresponding to amino acids 1142–1153 of the insulin receptor (IR) kinase domain that was synthesized to contain phosphotyrosine at residues 1146, 1150 and 1151. The procedure used and results obtained are briefly described below.

Human, recombinant PTP1B (hPTP1B) was prepared as described by Goldstein (see Goldstein et al. *Mol. Cell. Biochem.* 109, 107, 1992). The enzyme preparation used was stored in microtubes containing 4000–10000 μg/ml protein in 10 mM Tris-HCl, 0.2 mM EDTA, 25 mM NaCl, 50% glycerol and 3mM DTT.

Measurement of PTPase activity. The malachite green-ammonium molybdate method is used for the nanomolar detection of liberated phosphate by recombinant PTP1B as described (Lanzetta et al. *Anal. Biochem.* 100, 95, 1979). The assay was adapted for use with a 96-well microtiter platereader. The test procedure uses a dodecaphosphopeptide (TRDIpYETDpYpYRK) custom synthesized by AnaSpec, Inc. (San Jose, Calif.) corresponding to amino acids 1142–1153 of the insulin receptor β-subunit. Phosphotyrosine is incorporated at residues 1146, 1150, and 1151 as indicated. The recombinant hPTP1B is diluted to 1 μg/ml with buffer containing 10 mM Tris-HCl pH 7.4, 10 mM β-mercaptoethanol, and 30% Glycerol yielding an approximate activity of 10000–20000 nmoles inorganic phosphate released/min/mg protein. The diluted enzyme (166.5 μl) is added to 621 μl of reaction buffer containing 81.83 mM HEPES pH 7.4, 1.1 mM β-mercaptoethanol and then pre-incubated for 5 min at 37° C. with 2.5 μl of either test compound or DMSO as control. The dephosphorylation reaction is initiated by adding an aliquot (39.5 μl) of the recombinant hPTP1B:inhibitor preincubation mixture to the appropriate wells of a 96-well microtiter plate containing 10.5 μl of IR triphosphopeptide substrate pre-equilibrated to 37° C. A final concentration of 50 mM HEPES, 8.46 mM β-mercaptoethanol and 50 μM IR triphosphopeptide is achieved in the well. After 5 min at 37° C., the reaction is terminated by the addition of 200 μl of malachite green-ammonium molybdate-Tween 20 stopping reagent (MG/AM/Tw). The stopping reagent consists of 3 parts 0.45% malachite green hydrochloride, 1 part 4.2% ammonium molybdate tetrahydrate in 4 N HCl and 0.5% Tween 20. Sample blanks are prepared by the addition of 200 μl MG/AM/Tw to wells containing 10.5 μl of IR triphosphopeptide substrate followed by the addition of 39.5 μl of the recombinant enzyme preincubated with either DMSO or drug. The colored product is allowed to develop at room temperature for 25 min. Sample absorbance is determined at 650 nm using a 96-well microtiter platereader (Bio-Tek). Samples and blanks are prepared in quadruplicates.

Calculations: PTPase activity, expressed as nmoles of inorganic phosphate released/min/mg protein, is quantified by extrapolation from a standard curve using known quantities of potassium phosphate. Inhibition of recombinant hPTP1B by test compounds is calculated as a percentage of control (i.e. activity achieved in the presence of DMSO alone). A four parameter, non-linear logistic regression of PTPase activities using SAS release 6.08, PROC NLIN, is used for determining $IC_{50}$ values of test compounds. The following results were obtained.

| Example | IC50 (μM) |
| --- | --- |
| 1 | 5.8% inhibition @ 2.5 μM |
| 2 | 1.260 |
| 3 | 34.90% inhibition @ 2.5 μM |
| 4 | 0.354 |
| 5 | 65.52% inhibition @ 2.5 μM |
| 6 | 26.93% inhibition @ 2.5 μM |
| 7 | 0.409 |
| 8 | 1.120 |
| 9 | 0.987 |
| 10 | 34.44% inhibition @ 2.5 μM |
| 11 | 42.82% inhibition @ 1.0 μM |
| 12 | 64.19% inhibition @ 2.5 μM |
| Phenylarsine oxide (reference standard) | 39.7 |
| Sodium orthovanadate (reference standard) | 244.8 |
| Ammonium molybdate tetrahydrate (reference standard) | 8.7 |

Based on the results obtained in the standard pharmacological test procedure, representative compounds of this invention have been shown to inhibit PTPase activity and are therefore useful in treating metabolic disorders related to insulin resistance or hyperglycemia, typically associated with obesity or glucose intolerance. More particularly, the compounds of this invention useful in the treatment or inhibition of type II diabetes, and in modulating glucose levels in disorders such as type I diabetes. As used herein, the term modulating means maintaining glucose levels within clinically normal ranges.

Effective administration of these compounds may be given at a daily dosage of from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

The following procedures describe the preparation of representative examples of this invention.

EXAMPLE 1

(5'-Benzoyl-[1,1';3',1"]terphenyl-2'-yloxy)-acetic acid sodium salt

Step 1

(4-Hydroxy-3,5-diiodo-phenyl)-phenyl-methanone

At 0° C., to a stirred solution containing 4-hydroxybenzophenone (2.00 g, 10.1 mmol) and sodium hydroxide (0.807 g, 20.2 mmol) in MeOH (66 mL) was added portionwise iodine (6.40 g, 25.2 mmol) over a period of 45 minutes. After the addition was completed, the reaction was stirred for 2.5h. The reaction was adjusted to pH 1 with 2N HCl, diluted with $H_2O$ and extracted with ether. The ethereal extracts were washed sequentially with 10% aq. sodium thiosulfate (3×), with $H_2O$ (3×), with brine (3×), dried ($MgSO_4$) and concentrated. Purification on Biotage KP-Sil eluting with 100% $CHCl_3$ gave 1.32 g (29%) of the title compound as a white solid. $^1H$ NMR consistent.

Step 2

{4-[(2-Methoxyethoxy)methoxyl]-3,5-diiodo-phenyl}-phenyl-methanone

At 0° C., to a stirred suspension of 60% sodium hydride/mineral oil (0.283 g, 7.08 mmol) in THF (6.98 mL) was added a solution of (4-hydroxy-3,5-diiodo-phenyl)-phenyl-methanone (2.45 g, 5.44 mmol) in THF (5.33 mL). After the addition was completed the reaction was stirred of 0.5 h. To the reaction was added a solution of MEM chloride (0.994 mL, 8.71 mmol) in THF (8.64 mL) and the reaction was stirred for 1.5 h. The reaction was quenched with 0.1N KOH and extracted with ether. The ethereal extracts were washed with sequentially with $H_2O$ (3×), with brine (3×), dried ($MgSO_4$) and concentrated to give 3.00 g of the title compound as a yellow oil. $^1H$ NMR consistent.

Step 3

(2'-(2-Methoxyethoxy)methoxy)-[1,1';3'1"]terphenyl-5'-yl)-phenyl-methanone

At ambient temperature, to a stirred solution containing phenyl boronic acid (1.19 g, 9.77 mmol), barium hydroxide octahydrate (4.20 g, 13.3 mmol) and palladium (II) acetate (20.0 mg, 0.0888 mmol) in DME:$H_2O$ (64 mL, 6:1) was added a solution of {4-[(2-methoxyethoxy)methoxy]-3,5-diiodo-phenyl}-phenyl-methanone (2.46 g, 4.44 mmol) in DME:$H_2O$ (25 mL, 6:1). The reaction was stirred at ambient temperature for 2 h, then heated to 80° C. for 24 h. The reaction was cooled to ambient temperature diluted with ether (220 mL), washed sequentially with sat. aq. $NaHCO_3$ (3×), with brine (3×), dried ($MgSO_4$) and concentrated. The crude product was purified on Biotage KP-Sil eluting with 15% EtOAc/ pet. ether to give 0.97 g (50%) of the title compound as a white solid. $^1H$ NMR consistent.

Step 4

(2'-Hydroxy-[1,1';3'1"]terphenyl-5'-yl)-phenyl-methanone

At ambient temperature, to a stirred solution of (2'-(2-methoxyethoxy)methoxy)-[1,1';3'1"]terphenyl-5'-yl)-phenyl-methanone (0.97 g, 2.21 mmol) in $CH_2Cl_2$ (10 mL) was added trifluoroacetic acid (10 mL). After 4h, the reaction was diluted with ether (90 mL), washed sequentially with $H_2O$ (3×), with pH 7 buffer (3×), with brine (3×), dried ($MgSO_4$) and concentrated. The crude product was combined with product from an identical experiment and purified on Biotage KP-Sil eluting with 15% EtOAc/pet. ether to give 1.0 g of the title compound as a white solid, mp 145° C. $^1H$ NMR (DMSO-d6)δ 7.35–7.39 (m, 2H), 7.43–7.47 (m, 4H), 7.52–7.57 (m, 6H), 7.60–7.65 (m, 3 H), 7.75–7.77 (m, 2H), 9.35 (s, 1H). IR (KBr) 3200, 3050, 1650, 1600, 1340 and 1250 $cm^{-1}$. mass spectrum (EI) m/z 350 (M+). Anal. Calcd. for $C_{25}H_{18}O_2$ 1.0$H_2O$: C, 81.50; H, 5.47; N, 0.00. Found: C, 81.45; H, 5.13; N, 0.06.

Step 5

Methyl-(5'-benzoyl-[1,1';3',1"]terphenyl-2'-yloxy)-acetate

At 0° C., to a stirred solution containing (2'-hydroxy-[1,1';3'1"]terphenyl-5'-yl)-phenyl-methanone (0.204 g, 0.583 mmol), methyl glycolate (49.4 µL, 0.641 mmol) and triphenylphosphine (0.168 g, 0.641 mmol) in THF (5.83 mL) was added dropwise diethylazodicarboxylate (101 µL, 0.641 mmol). After 3 days, the reaction was quenched with pH7 buffer (50 mL) and extracted with ether. The ethereal extracts were washed sequentially with sat. aq. $NaHCO_3$ (3×), with brine (3×), dried ($MgSO_4$) and concentrated. The crude product was purified on Biotage KP-Sil eluting with 10% acetone/hexane to give 0.142 g (58%) of the title compound. $^1H$ NMR consistent.

Step 6

(5'-Benzoyl-[1,1';3',1"]terphenyl-2'-yloxy)-acetic acid sodium salt

At ambient temperature, to a stirred solution containing methyl-(5'-benzoyl-[1,1';3', 1"]terphenyl-2'-yloxy)-acetate (0.134 g, 0.318 mmol) in THF:MeOH (1:1, 3.18 5 mL) was added 1N KOH (0.635 mL). After 1 h, the reaction was quenched with 1N HCl (20 mL) and extracted with EtOAc.

The organic extracts were dried (MgSO$_4$) and concentrated. The free acid was purified on Biotage KP-Sil eluting with EtOAc:MeOH:H$_2$O (30:2:1). The sodium salt was prepared by dissolving the free acid in MeOH and treating with 25% wt. Na$^+$OMe/MeOH (53 mg). Crystallization from ether gave 0.075 g (55%) of the title compound as a white solid, mp>225° C. $^1$H NMR (DMSO-d6) δ 3.52 (s, 2H), 7.32–7.42 (m, 6H), 7.57 (t, 2H), 7.62–7.77 (m, 7H), 7.79 (d, 2H). IR (KBr) 3400, 3100, 1620, 1410 and 1260 cm$^{-1}$. mass spectrum (+ESI) m/z 409 (M+H), 431 (M+Na).

EXAMPLE 2

4-(5'-Benzoyl-[1,1';3',1"]terphenyl-2'-yloxymethyl)-2-hydroxy-benzoic acid

Step 1

2-Acetoxy-4-(hydroxymethyl) benzoic acid methyl ester

A solution containing 2-acetoxy-4-(bromomethyl) benzoic acid methyl ester (1.34g, 4.67 mmol, RN 13339-10-1) and sodium formate (0.795 g, 11.7 mmol) In EtOH:DMSO:H$_2$O (2:2:1, 93 mL) was heated at 100° C. for 16 h. The reaction was cooled to ambient temperature, diluted with 10% CH$_2$Cl$_2$/EtOAc (100 mL), washed with brine (3×), dried (Na$_2$SO$_4$) and concentrated. The crude product was purified on Biotage KP-Sil eluting with 20% acetone/hexane to give 0.518 g (49%) of the title compound as a clear oil. $^1$H NMR (DMSO-d6) δ 2.28 (s, 3H), 3.80 (s, 3H), 4.57 (d, 2H), 5.45 (br, t, 1H), 7.16 (s, 1H), 7.33 (d, 1H), 7.91 (d, 1H).

Step 2

4-(5'-Benzoyl-[1,1';3',1"]terphenyl-2'-yloxymethyl)-2-acetoxy-benzoic acid methyl ester The title compound was prepared according to the procedure in Example 1, step 5 using 2-acetoxy-4-(hydroxymethyl) benzoic acid methyl ester (0.256 g, 1.14 mmol), (2'-hydroxy-[1,1';3'1"]terphenyl-5'-yl)-phenyl-methanone (0.400 g, 1.14 mmol), triphenylphosphine (0.329 g, 1.26 mmol) and diethylazodicarboxylate (197 μL, 1.26 mmol) in THF (11.4 mL). Purification on Biotage KP-Sil eluting with 10% acetone/hexane gave 0.533 g (84%) of the title compound. $^1$H NMR consistent.

Step 3

4-(5 '-Benzoyl-[1,1';3',1"]terphenyl-2'-yloxymethyl)-2-hydroxy-benzoic acid

At ambient temperature, to a stirred solution of 4-(5'-benzoyl-[1,1';3',1"]terphenyl-2'-yloxymethyl)-2-acetoxy-benzoic acid methyl ester (0.527 g, 0.946 mmol) in MeOH:THF (1:1,15 mL) was added K$_2$CO$_3$ (0.261 g, 1.89 mmol). After 1 h, to the reaction was added 1N NaOH (5 mL) and the reaction was heated at 100° C. for 4 h. The reaction was cooled to ambient temperature, acidified with 1N HCl and extracted with EtOAc. The organic extracts were dried (Na$_2$SO$_4$) and concentrated. Recrystallization from ether/pet. ether gave 0.261g (55%) of the title compound as a white solid, mp 217–220'C. $^1$H NMR (DMSO-d6) δ 4.25 (s, 2H), 6.29 (dd, 1H), 6.34 (d, 1H), 7.38–7.48 (m, 6H), 7.53–7.69 (m, 8H), 7.72 (s, 2H), 7.82 (d, 2H). IR (KBr) 3050, 1675, 1620, 1575 and 1210 cm$^{-1}$. mass spectrum (EI) m/z 500 (M+). Anal. Calcd. for C$_{33}$H$_{24}$O$_5$ H$_2$O: C,76.43; H,5.05; N,0.00. Found: C,76.75; H,4.82; N,0.03.

EXAMPLE 3

2-Acetoxy-5-(4-benzoyl-2,6-diiodo-phenoxymethyl)-benzoic acid methyl ester

The title compound was prepared according to the procedure in Example 1, step 5 using 2-acetoxy-4-(hydroxymethyl) benzoic acid methyl ester (0.109 g, 0.484 mmol), (4-hydroxy-3,5-diiodo-phenyl)-phenyl-methanone (0.218 g, 0.484 mmol), triphenylphosphine (0.140 g, 0.533 mmol) and diethylazodicarboxylate (83.5 μL, 0.533 mmol) in benzene (4.84 mL). Purification on Biotage KP-Sil eluting with a 10, 15 & 20% EtOAc/pet. ether gave 0.173 g (54%) of the title compound as a white solid, mp 132–135° C. $^1$H NMR (DMSO-d6) δ 2.30 (s, 3H), 3.83 (s, 3H), 5.09 (s, 2H), 7.35 (d, 1H), 7.58 (t, 2H), 7.69–7.75 (m, 3H), 7.92 (dd, 1H), 8.13 (d, 2H), 8.19 (d, 1 H). IR (KBr) 2950, 1760, 1220, 1660 and 1275 cm$^{-1}$. mass spectrum (+FAB) m/z 657 (M+H), 679 (M+Na).

EXAMPLE 4

4-(5'-Benzoyl-[1,1';3',1"]terphenyl-2'-yloxysulfonyl)-2-hydroxy-benzoic acid

At ambient temperature, to a stirred solution of (2'-hydroxy-[1,1';3',1"]terphenyl-5'-yl)-phenyl-methanone (2.02 g, 5.77 mmol) in THF (55 mL) was added portionwise 4-chlorosulphonyl-2-hydroxybenzoic acid (2.70 g, 11.4 mmol, RN 98273-15-5) while maintaining the pH at 8 with the simultaneous addition of 0.5M aq. NaHCO$_3$. After the addition was complete the reaction was stirred for 3.5 h. To the reaction was added 4-chlorosulphonyl-2-hydroxybenzoic acid (2.70 g, 11.4 mmol) while maintaining the pH at 8 with the simultaneous addition of 0.5 M aq. NaHCO$_3$. After the addition was complete the reaction was stirred for 18 h. To the reaction was added 4-chlorosulphonyl-2-hydroxybenzoic acid (2.05 g, 8.66 mmol) while maintaining the pH at 8 with the simultaneous addition of 0.5M aq. NaHCO$_3$. After 2h, the reaction was quenched with 2N HCl (25 mL), extracted with EtOAc and concentrated. Purification by preparative HPLC (C18, eluting with 75% CH$_3$CN/H$_2$O containing 0.1% TFA) and crystallization from EtOAc/hexane gave 0.65 g (20%) of the title compound as a yellow solid, mp 217° C.; $^1$H NMR (DMSO-d6) δ 6.60 (d, 1H), 6.74 (dd, 1H), 7.30–7.35 (m, 6H), 7.46–7.49 (m, 4H), 7.57–7.61 (m, 3H), 7.68–7.72 (m, 3H), 7.83–7.85 (m, 2H). mass spectrum (EI) ml/z 550 (M+). Anal. Calcd. for C$_{32}$H$_{22}$O$_7$S 0.4H$_2$O: C,68.91; H,4.12; N,0.00. Found: C,68.87; H,4.10; N,0.16.

EXAMPLE 5

4-(5'-Benzoyl-[1,1';3',1"]terphenyl-2'-yloxysulfonyl)-2-hydroxy-benzoic acid ethyl ester A stirred solution containing 4-(5'-benzoyl-[1,1';3',1"] terphenyl-2'-yloxysulfonyl)-2-hydroxy-benzoic acid (0.106 g, 0.192 mmol), tributylamine (0.110 mL, 0.462 mmol), ethanol (0.0677 mL, 1.15 mmol) and 2-chloro-1-methyl pyridinium iodide (0.0607 g, 0.231 mmol) in CH$_2$Cl$_2$ (2 mL) was refluxed for 18 h. The reaction was cooled to ambient temperature, quenched with 1N HCl (20 mL) and extracted with EtOAc. The organic extracts were successively washed with 1N HCl (3×), with brine (3×), dried (MgSO$_4$) and concentrated. Purification on Biotage KP-Sil eluting with 20% acetone/hexane gave 0.039g (35%) of the title compound as a white solid, mp 75–85° C. $^1$H NMR (DMSO-d6) δ 1.36 (t, 3H), 4.38 (q, 2H), 6.67 (d, 1H), 6.73 (dd, 1H), 7.30–7.36 (m, 6H), 7.45–7.52 (m, 5H), 7.57–7.61 (m, 2H), 7.68–7.71 (m, 3H), 7.84 (d, 2H), 10.60 (s, 1H). mass spectrum (EI) m/z 578 (M+). Anal. Calcd. for C$_{34}$H$_{26}$O$_7$S 0.5H$_2$O: C,69.49; H,4.63; N,0.00. Found: C,69.38; H,4.76; N,0.10.

EXAMPLE 6

2-Hydroxy-4-[4-(4-methoxy-benzoyl)-phenoxysulfonyl]-benzoic acid

The title compound was prepared according to the procedure in Example 4 using commercial 4-hydroxy-4'methoxybenzophenone (0.206 g, 0.903 mmol) and 4-chlorosulphonyl-2-hydroxybenzoic acid (0.427 g, 1.81 mmol) in THF (5 mL). Purification by preparative HPLC (C18, eluting with 60% CH$_3$CN/H$_2$O containing 0.1% TFA) and crystallization from EtOAc/hexane gave 0.21 g (54%) of the title compound as an off white solid, mp 73–75° C.; $^1$H NMR (DMSO-d6) δ 3.85 (s, 3H), 7.07 (d, 2H), 7.24 (d, 2H), 7.36–7.38 (m, 2H), 7.68–7.73 (m, 4H), 7.99 (s, 1 H). IR (KBr) 3400, 1700, 1650, 1000 and 1260 cm$^{-1}$. mass spectrum (–ESI) m/z 427 (M–H).

EXAMPLE 7

4-[2,6-Diiodo-4-(4-methoxy-benzoyl)-phenoxysulfonyl]-2-hydroxy-benzoic acid

Step 1

(4-Hydroxy-3,5-diiodo-phenyl)-(4-methoxy-phenyl)-methanone

The title compound was prepared according to the procedure in Example 1, step 1 using commercial 4-hydroxy-4'methoxybenzophenone (2.50 g, 11.0 mmol), iodine (6.95 g, 27.4 mmol) and sodium hydroxide (0.876 g, 21.0 mmol) in MeOH (72.3 mL). Purification on Biotage KP-Sil eluting with CHCl$_3$ gave 1.47 g (28%) of the title compound as a yellow solid, mp 177–178° C. $^1$ H NMR (DMSO-d6) δ 3,52 (s, 3H), 7.06–7.10 (m, 2H), 7.68–7.71 (m, 2H), 8.00 (s, 2H), 10.4 (br s, 1H). IR (KBr) 3400, 3100, 1640, 1600 and 1240 cm$^{-1}$. mass spectrum (EI) m/z 480 (M+).

Step 2

4-[2,6-Diiodo-4-(4-methoxy-benzoyl)-phenoxysulfonyl]-2-hydroxy-benzoic acid

The title compound was prepared according to the procedure in Example 4 using (4-hydroxy-3,5-diiodo-phenyl)-(4-methoxy-phenyl)-methanone (0.202 g, 0.421 mmol) and 4-chlorosulphonyl-2-hydroxybenzoic acid (0.398 g, 1.68 mmol) in THF (5 mL). Purification by preparative HPLC (C$_{18,}$ eluting with 70% CH$_3$CN/H$_2$O containing 0.1% TFA) gave 0.045 g (16%) of the title compound as a white solid, mp 214–215° C. $^1$H NMR (DMSO-d6) δ 3.86 (s, 3H), 7.11 (d, 2H), 7.44–7.48 (m, 2H), 7.73 (d, 2 H), 8.04–8.07 (m, 3H). IR (KBr) 3400, 3050, 1690, 1600, 1260 and 1175 cm$^{-1}$. mass spectrum (–ESI) m/z 679 (M–H). Anal. Calcd. for C$_{21}$H$_{14}$I$_2$O$_8$S: C,37.08; H,2.07; N,0.00. Found: C,37.43; H,2.24; N,0.00.

EXAMPLE 8

2-Hydroxy-4-[5'-(4-methoxy-benzoyl)-[1,1':3',1"]terphenyl-2'-yloxysulfonyl)-benzoic acid Step 1

{4-[(2-Methoxyethoxy)methoxyl]-3,5-diiodo-phenyl}-(4-methoxy-phenyl)-methanone

The title compound was prepared according to the procedure in Example 1, step 2 using (4-hydroxy-3,5-diiodo-phenyl)-(4-methoxy-phenyl)-methanone (1.16 g, 2.42 mmol), 60% sodium hydride/mineral oil (0.126 g, 3.14 mmol), MEM chloride (0.442 15 mL, 3.87 mmol) in THF (11 mL) to give 1.09 g (80%) of the title compound as a white solid. $^1$H NMR consistent.

Step 2

(2'-(2-Methoxyethoxy)methoxy)-[ 1,1';3',1"]terphenyl-5'-yl)-(4-methoxy-phenyl)-methanone The title compound was prepared according to the procedure in Example 1, step 3 using {4-[(2-methoxyethoxy)methoxy]-3,5-diiodo-phenyl}-(4-methoxy-phenyl)-methanone (1.09 g, 1.87 mmol), phenyl boronic acid (0.501 g, 4.11 mmol), barium hydroxide octahydrate (1.77 g, 5.61 mmol) and palladium (II) acetate (8.4 mg, 0.0379 mmol) in DME:H$_2$0 (47 mL, 6:1). Purification on Biotage KP-Sil eluting with a 15 & 20% EtOAc/pet. ether step gradient gave 0.67 g (74%) of the title compound as a clear oil. $^1$H NMR consistent.

Step 3

2'-Hydroxy-[1, 1';3'1"]terphenyl-5'-yl)-(4-methoxy-phenyl)-methanone

The title compound was prepared according to the procedure in Example 1, step 4 using (2'-(2-methoxyethoxy)methoxy)-[1,1';3'1"]terphenyl-5'-yl)-(4-methoxy-phenyl)-methanone (0.67 g, 1.43 mmol) and trifluoroacetic acid (10 mL) in CH$_2$Cl$_2$ (10 mL) to give the title compound as a white solid, mp 189–190° C. $^1$H NMR (DMSO-d6) δ 3.83 (s, 3H), 7.06 (d, 2H), 7.35 (br. t, 2H), 7.44 (t, 4H), 7.52–7.58 (m, 6H), 7.77 (d, 2H), 9.24 (br. s, 1H). IR (KBr) 3450, 3050, 1640, 1600, 1250 and 1210 cm$^{-1}$. mass spectrum (–ESI) m/z 379 (M–H). Anal. Calcd. for C$_{26}$H$_{20}$O$_3$ 0.6H$_2$O: C,79.82; H,5.46; N,0.00. Found: C,79.80; H,5.36; N,0.00.

Step 4

2-Hydroxy-4-[5'-(4-methoxy-benzoyl)-[1,1';3',1"]terphenyl-2'-yloxysulfonyl)-benzoic acid The title compound was prepared according to the procedure in Example 4 using 2'-hydroxy-[1,1';3'1"]terphenyl-5'-yl)-(4-methoxy-phenyl)-methanone (0.300 g, 0.789 mmol) and 4-chlorosulphonyl-2-hydroxybenzoic acid (0.744 g, 3.14 mmol) in THF (8 mL). Crystallization from EtOAc/hexane gave 0.28 g of the title compound as a white solid, mp>225° C. $^1$H NMR (DMSO-d6) δ 3.84 (s, 3H), 6.56 (d, 1H), 6.68 (dd, 1H), 7.09 (d, 2H), 7.28–7.34 (m, 6H), 7.46 (dd, 4H), 7.57 (d, 1H), 7.65 (s, 2H), 7.83 (d, 2H). IR (KBr) 3450, 3050, 1675, 1600, 1260 and 1160 cm$^{-1}$. mass spectrum (–ESI) m/z 579 (M–H). Anal. Calcd. for C$_{33}$H$_{24}$O$_8$S: C,68.27; H,4.17; N,0.00. Found: C,67.90; H,4.34; N,0.24.

EXAMPLE 9

4-(4-Benzoyl-2,6-di -thiophen-3-yl-phenoxysulfonyl)-2-hydroxy-benzoic acid

Step 1

{4-[(2-Methoxyethoxy)methoxyl]-3,5-dithiophen-3-yl}-phenyl-methanone

The title compound was prepared according to the procedure in Example 1, step 3 using {4-[(2-methoxyethoxy)methoxy]-3,5-diiodo-phenyl}-phenyl-methanone (2.00 g, 3.61 mmol), thiophene-3-boronic acid (2.04 g, 15.9 mmol), barium hydroxide octahydrate (6.84 g, 21.7 mmol) and palladium (II) acetate (32.4 mg, 0.145 mmol) in DME:H$_2$O (70 mL, 6:1) to give 1.65 g of the title compound used without any additional purification. $^1$H NMR consistent.

Step 2

(4-Hydroxy-3,5-dithiophen-3-yl)-phenyl -methanone

The title compound was prepared according to the procedure in Example 1, step 4 using {4-[(2-methoxyethoxy)methoxy]-3,5-dithiophen-3-yl}-phenyl-methanone (1.65 g) and trifluoroacetic acid (20 mL) in CH$_2$Cl$_2$ (20 mL). Purification on Biotage KP-Sil eluting with a 10 & 15% EtOAc/pet. ether step gradient gave 0.71 g (54%) the title compound as an off white solid, mp 140–145° C. $^1$H NMR (DMSO-d6) δ 7.44 (dd, 2 H), 7.57 (t, 2H), 7.63–7.66 (m, 3H), 7.73 (s, 2H), 7.77 (dd, 2H), 7.81–7.82 (m, 2H), 7.50 (s, 1H). IR (KBr) 3500, 3050, 1640, 1600 and 1300 cm$^{-1}$. mass spectrum (EI) m/z 362 (M+). Anal. Calcd. for C$_{21}$H$_{14}$O$_2$S$_2$ 0.6H$_2$O: C,67.57; H,4.10; N,0.00. Found: C,67.50; H,3.94; N,0.11.

Step 4

4-(4-Benzoyl-2,6-di-thiophen-3-yl-phenoxysulfonyl)-2-hydroxy-benzoic acid

The title compound was prepared according to the procedure in Example 4 using (4-hydroxy-3,5-dithiophen-3-yl)-phenyl-methanone (0.205 g, 0.566 mmol) and 4-chlorosulphonyl-2-hydroxybenzoic acid (0.348 g, 1.47 mmol) in THF. Purification by preparative HPLC (C$_{18,}$ eluting with 75% CH$_3$CN/H$_2$O containing 0.1% TFA), followed by crystallization from EtOAc/hexane gave 0.15 g (47%) of the title compound as a white solid, mp>225° C. $^1$H NMR (DMSO-d6) δ 6.74 (br. s, 1H), 6.81 (br. d, I H), 7.30 (dd, 2H), 7.49–7.51 (m, 2H), 7.59 (t, 2H), 7.67–7.74 (m, 6H), 7.82 (d, 2H). IR (KBr) 3400, 3050, 1740, 1630, 1490 and 1240 cm$^{-1}$. mass spectrum (EI) m/z 562 (M+). Anal. Calcd. for C$_{28}$H$_{18}$O$_7$S$_3$ 0.4H$_2$O: C,59.02; H,3.33; N,0.00. Found: C,58.97; H,3.37; N,0.11.

EXAMPLE 10
4-(5'-Benzoyl-[1,1';3',1"]terphenyl-2'-yloxysulfonyl)-benzoic acid The title compound was prepared according to the procedure in Example 4 using (2'-hydroxy-[1,1';3'1"]terphenyl-5'-yl)-phenyl-methanone (0.205 g, 0.571 mmol) and commercial 4-(chlorosulphonyl)-benzoic acid (0.252 g, 1.14 mmol) in THF. Purification by preparative HPLC (C18, eluting with 75% CH$_3$CN/H$_2$O containing 0.1% TFA), followed by crystallization from EtOAc/hexane gave 0.05 g (16%) of the title compound as a white solid, mp 217–218° C. $^1$H NMR (DMSO-d6) δ 7.27–7.32 (m, 8H), 7.43–7.45 (m, 4H), 7.57 (t, 2H), 7.67–7.73 (m, 5H), 7.83 (dd, 2H) 13.5 (br s, 1H). IR (KBr) 3400, 3050, 1750, 1660, 1390 and 1200 cm$^{-1}$. mass spectrum (EI) m/z 534 (M+). Anal. Calcd. for C$_{32}$H$_{22}$O$_6$S H$_2$O: C,69.55; H,4.38; N,0.00. Found: C,69.28; H,4.26; N,0.21.

EXAMPLE 11
4-[5-(2-Chloro-benzoyl)-biphenyl-2-yloxysulfonyl]-2-hydroxy-benzoic acid
Step 1
(2-Chloro-phenyl)-(6-hydroxy-biphenyl-3-yl)-methanone At ambient temperature, to a stirred suspension of aluminum chloride (2.0 g, 15.0 mmol) in CH$_2$Cl$_2$ (20 mL) was added 2-phenylphenol (1.28 g, 7.53 mmol). After 30 min, the reaction was cooled to 0° C. To the reaction was added dropwise a solution of 2-chlorobenzoyl chloride (0.94 mL, 7.42 mmol) in CH$_2$Cl$_2$ (20 mL). The reaction was allowed to warm to ambient temperature and stirred overnight. The reaction was quenched into crushed ice (100 g) diluted with sat. aq. KH$_2$PO$_4$ (100 mL) and extracted with CH$_2$Cl$_2$. The organic extracts were dried (Na$_2$SO$_4$) and concentrated. The crude product was purified on Biotage KP-Sil eluting with a 3 & 10% EtOAc/pet. ether step gradient to give 0.5g (21%) of the title compound as an off white solid, mp 194–198° C. $^1$H NMR (DMSO-d6) δ 7.07 (dd, 1H), 7.33 (tt, 1H), 7.40 (tt, 2H), 7.46–7.49 (m, 4H), 7.51–7.59 (m, 4H), 10.8 (s, 1H). mass spectrum (EI) m/z 308 (M+).
Step 2
4-[5-(2-Chloro-benzoyl)-biphenyl-2-yloxysulfonyl]-2-hydroxy-benzoic acid The title compound was prepared according to the procedure in Example 4 using (2-chloro-phenyl)-(6-hydroxy-biphenyl-3-yl)-methanone (0.300 g, 0.972 mmol) and 4-chlorosulphonyl-2-hydroxybenzoic acid (0.436 g, 1.84 mmol) in THF. Purification by preparative HPLC (C$_{18}$, eluting with CH$_3$CN/H$_2$O containing 0.1 % TFA), followed by crystallization from EtOAc/hexane gave 0.34 g (69%) of the title compound as a tan solid, mp 101–102° C. $^1$H NMR (DMSO-d6) δ 6.82 (d, 1H), 6.85 (dd, 1H), 7.14–7.16 (m, 2H), 7.27–7.33 (m, 3H), 7.52–7.54 (m, 1H), 7.58–7.65 (m, 5H), 7.71 (d, 1H), 7.81 (dd, 1H). IR (KBr) 3400, 3050, 1675, 1390 and 1190 cm$^{-1}$. mass spectrum (EI) m/z 508 (M +). Anal. Calcd. for C$_{26}$H$_{17}$ClO$_7$S 0.5H$_2$O: C,60.29; H,3.50; N,0.00. Found: C,60.35; H,3.68; N,0.14.

EXAMPLE 12
4-(4-Benzoyl-2,6-diiodo-phenoxysulfonyl)-2-hydroxy-benzoic acid

The title compound was prepared according to the procedure in Example 4 using (4-hydroxy-3,5-diiodo-phenyl)-phenyl-methanone (0.346 g, 0.768 mmol) and 4-chlorosulphonyl-2-hydroxybenzoic acid (0.928 g, 3.92 mmol) in THF. Purification On Biotage KP-Sil, eluting with 10% MeOH/CHCl$_3$ followed by crystallization from EtOAc/hexane gave 0.15 g (30%) of the title compound as an orange solid, mp 190° C. $^1$H NMR (DMSO-d6) δ 7.22–7.35 (m, 2H), 7.58 (t, 2H), 7.69–7.75 (m, 3H), 7.95 (d, 1H), 8.10 (s, 2H). IR (KBr) 3400, 3100, 1660, 1280 and 1180 cm$^{-1}$. mass spectrum (+FAB) m/z 651 (M+H). Anal. Calcd. for C$_{20}$H$_{12}$I$_2$O$_7$S 0.5H$_2$O: C,36.44; H,1.99; N,0.00. Found: C,36.50; H,2.16; N,0.09.

What is claimed is:

1. A method of treating metabolic disorders mediated by insulin resistance or hyperglycemia in a mammal in need thereof which comprises administering to said mammal, a compound of formula I having the structure

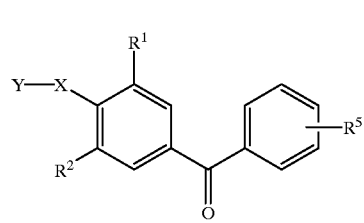

(I)

wherein
Y is

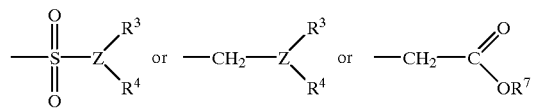

$R^1$ and $R^2$ are each, independently, hydrogen, alkyl of 1–6 carbon atoms, halogen, perfluoroalkyl of 1–6 carbon atoms, cycloalkyl of 3–8 carbon atoms, thienyl, furyl, phenyl or phenyl mono-, di- or tri-substituted with trifluoromethyl, chloro, methoxy, or trifluoromethoxy;

$R^3$ and $R^4$ are each, independently, hydrogen, carboxyl, hydroxyl, hydoxyalkyl of 1–6 carbon atoms, hydroxyalkanoyl of 1–6 carbon atoms, aryloxycarbonyl of 7–13 carbon atoms, alkoxycarbonyl of 2–7 carbon atoms, perfluoroalkoxycarbonyl of 2–7 carbon atoms, alkyl of 1–6 carbon atoms, perfluoroalkyl of 1–6 carbon atoms, aminoalkyl of 1–6 carbon atoms, alkylamino of 1–6 carbon atoms, dialkylamino of 1–6 carbon atoms per alkyl group, tetrazolyl, mercapto, alkylsulfanyl of 1–6 carbon atoms, nitrile, nitro, amino, —NHSO$_2$CF$_3$, carbamoyl, carboxyaldehyde, halogen, acyl of 1–6 carbon atoms, acylamino of 1–6 carbon atoms, 3-hydroxy-cyclobut-3-ene-4-yl-1,2-dione, pyridyl, isoxazolyl, pyrimidyl or pyrimidyl substituted with mercapto, tetronic acid, —OCOR$^8$, —OR$^8$ $R^8$ is aryl of 6–12 carbon atoms, aralkyl of 7–13 carbon atoms, monocyclic or bicyclic heteroaryl or a monocyclic or bicyclic heteroaralkyl, alkyl of 1–6 carbon atoms, perfluoroalkyl of 1–6 carbon atoms;

$R^5$ is hydrogen, alkyl of 1–6 carbon atoms, perfluoroalkyl of 1–6 carbon atoms, alkoxy of 1–6 carbon atoms, perfluoroalkoxy of 1–6 carbon atoms, or halogen;

X is —CH$_2$NR$^6$—, —NR$^6$—, or O;

R$^6$ and R$^7$ are each, hydrogen or alkyl of 1–6 carbon atoms;

Z is phenyl, naphthyl, or a pharmaceutically acceptable salt thereof.

2. A method of treating or inhibiting type II diabetes in a mammal in need thereof which comprises administering to said mammal, a compound of formula I having the structure

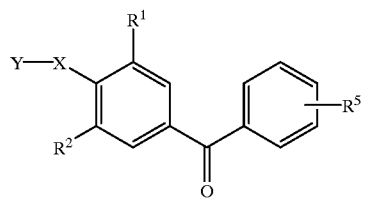
(I)

wherein

Y is

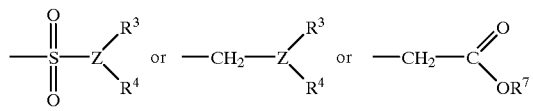

R$^1$ and R$^2$ are each, independently, hydrogen, alkyl of 1–6 carbon atoms, halogen, perfluoroalkyl of 1–6 carbon atoms, cycloalkyl of 3–8 carbon atoms, thienyl, furyl, phenyl or phenyl mono-, di- or tri-substituted with trifluoromethyl, chloro, methoxy, or trifluoromethoxy;

R$^3$ and R$^4$ are each, independently, hydrogen, carboxyl, hydroxyl, hydoxyalkyl of 1–6 carbon atoms, hydroxyalkanoyl of 1–6 carbon atoms, aryloxycarbonyl of 7–13 carbon atoms, alkoxycarbonyl of 2–7 carbon atoms, perfluoroalkoxycarbonyl of 2–7 carbon atoms, alkyl of 1–6 carbon atoms, perfluoroalkyl of 1–6 carbon atoms, aminoalkyl of 1–6 carbon atoms, alkylamino of 1–6 carbon atoms, dialkylamino of 1–6 carbon atoms per alkyl group, tetrazolyl, mercapto, alkylsulfanyl of 1–6 carbon atoms, nitrile, nitro, amino, —NHSO$_2$CF$_3$, carbamoyl, carboxyaldehyde, halogen, acyl of 1–6 carbon atoms, acylamino of 1–6 carbon atoms, 3-hydroxy-cyclobut-3-ene-4-yl-1,2-dione, pyridyl, isoxazolyl, pyrimidyl or pyrimidyl substituted with mercapto, tetronic acid, —OCOR$^8$, —OR$^8$ R$^8$ is aryl of 6–12 carbon atoms, aralkyl of 7–13 carbon atoms, monocyclic or bicyclic heteroaryl or a monocyclic or bicyclic heteroaralkyl, alkyl of 1–6 carbon atoms, perfluoroalkyl of 1–6 carbon atoms;

R$^5$ is hydrogen, alkyl of 1–6 carbon atoms, perfluoroalkyl of 1–6 carbon atoms, alkoxy of 1–6 carbon atoms, perfluoroalkoxy of 1–6 carbon atoms, or halogen;

X is —CH$_2$NR$^6$—, —NR$^6$—, or O;

R$^6$ and R$^7$ are each, hydrogen or alkyl of 1–6 carbon atoms;

Z is phenyl, naphthyl, or a pharmaceutically acceptable salt thereof.

3. A method of modulating glucose levels in a mammal in need thereof which comprises administering to said mammal, a compound of formula I having the structure

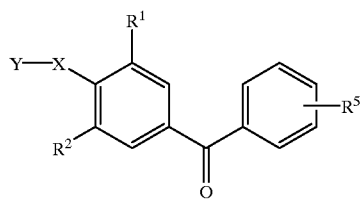
(I)

wherein

Y is

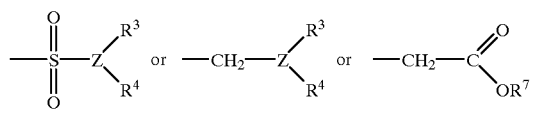

R$^1$ and R$^2$ are each, independently, hydrogen, alkyl of 1–6 carbon atoms, halogen, perfluoroalkyl of 1–6 carbon atoms, cycloalkyl of 3–8 carbon atoms, thienyl, furyl, phenyl or phenyl mono-, di- or tri-substituted with trifluoromethyl, chloro, methoxy, or trifluoromethoxy;

R$^3$ and R$^4$ are each, independently, hydrogen, carboxyl, hydroxyl, hydoxyalkyl of 1–6 carbon atoms, hydroxyalkanoyl of 1–6 carbon atoms, aryloxycarbonyl of 7–13 carbon atoms, alkoxycarbonyl of 2–7 carbon atoms, perfluoroalkoxycarbonyl of 2–7 carbon atoms, alkyl of 1–6 carbon atoms, perfluoroalkyl of 1–6 carbon atoms, aminoalkyl of 1–6 carbon atoms, alkylamino of 1–6 carbon atoms, dialkylamino of 1–6 carbon atoms per alkyl group, tetrazolyl, mercapto, alkylsulfanyl of 1–6 carbon atoms, nitrile, nitro, amino, —NHSO$_2$CF$_3$, carbamoyl, carboxyaldehyde, halogen, acyl of 1–6 carbon atoms, acylamino of 1–6 carbon atoms, 3-hydroxy-cyclobut-3-ene-4-yl-1,2-dione, pyridyl, isoxazolyl, pyrimidyl or pyrimidyl substituted with mercapto, tetronic acid, —OCOR$^8$, —OR$^8$ R$^8$ is aryl of 6–12 carbon atoms, aralkyl of 7–13 carbon atoms, monocyclic or bicyclic heteroaryl or a monocyclic or bicyclic heteroaralkyl, alkyl of 1–6 carbon atoms, perfluoroalkyl of 1–6 carbon atoms;

R$^5$ is hydrogen, alkyl of 1–6 carbon atoms, perfluoroalkyl of 1–6 carbon atoms, alkoxy of 1–6 carbon atoms, perfluoroalkoxy of 1–6 carbon atoms, or halogen;

X is —CH$_2$NR$^6$—, —NR$^6$—, or O;

R$^6$ and R$^7$ are each, hydrogen or alkyl of 1–6 carbon atoms;

Z is phenyl, naphthyl, or a pharmaceutically acceptable salt thereof.

4. A method according to claim 1, which is (5'-benzoyl-[1,1';3',1"]terphenyl-2'-yloxy)-acetic acid or a pharmaceutically acceptable salt thereof.

5. A method according to claim 1, which is 4-(5'-benzoyl-[1,1';3',1"]terphenyl-2'-yloxymethyl)-2-hydroxy-benzoic acid or a pharmaceutically acceptable salt thereof.

6. A method according to claim 1, which is 2-acetoxy-5-(4-benzoyl-2,6-diiodo-phenoxymethyl)-benzoic acid methyl ester.

7. A method according to claim 1, which is 4-(5'-benzoyl-[1,1';3',1"]terphenyl-2'-yloxysulfonyl)-2-hydroxy-benzoic acid or a pharmaceutically acceptable salt thereof.

8. A method according to claim 1, which is 4-(5'-benzoyl-[1,1';3',1"]terphenyl-2'-yloxysulfonyl)-2-hydroxy-benzoic acid ethyl ester or a pharmaceutically acceptable salt thereof.

9. A method according to claim 1, which is 2-hydroxy-4-[4-(4-methoxy-benzoyl)-phenoxysulfonyl]-benzoic acid or a pharmaceutically acceptable salt thereof.

10. A method according to claim 1, which is 4-[2,6-diiodo-4-(4-methoxy-benzoyl)-phenoxysulfonyl]-2-hydroxy-benzoic acid or a pharmaceutically acceptable salt thereof.

11. A method according to claim 1, which is 2-hydroxy-4-[5'-(4-methoxy-benzoyl)-[1,1';3',1"]terphenyl-2'-yloxysulfonyl)-benzoic acid or a pharmaceutically acceptable salt thereof.

12. A method according to claim 1, which is 4-(4-benzoyl-2,6-di-thiophen-3-yl-phenoxysulfonyl)-2-hydroxy-benzoic acid or a pharmaceutically acceptable salt thereof.

13. A method according to claim 1, which is 4-(5'-benzoyl-[1,1';3',1"]terphenyl-2'-yloxysulfonyl)-benzoic acid or a pharmaceutically acceptable salt thereof.

14. A method according to claim 1, which is 4-[5-(2-chloro-benzoyl)-biphenyl-2-yloxysulfonyl]-2-hydroxy-benzoic acid or a pharmaceutically acceptable salt thereof.

15. A method according to claim 1, which is 4-(4-benzoyl-2,6-diiodo-phenoxysulfonyl)-2-hydroxy-benzoic acid or a pharmaceutically acceptable salt thereof.

* * * * *